(12) United States Patent
Zemlicka et al.

(10) Patent No.: US 9,174,990 B2
(45) Date of Patent: Nov. 3, 2015

(54) 2-AMINO-9-[(2-HYDROXYMETHYL) CYCLOPROPYLIDENEMETHYL] PURINES AS ANTIVIRAL AGENTS

(75) Inventors: Jiri Zemlicka, Warren, MI (US); John C. Drach, Ann Arbor, MI (US); Xinchao Chen, Schenectady, NY (US)

(73) Assignees: WAYNE STATE UNIVERSITY, Detroit, MI (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1320 days.

(21) Appl. No.: 11/707,248

(22) Filed: Feb. 15, 2007

(65) Prior Publication Data
US 2007/0225302 A1    Sep. 27, 2007

Related U.S. Application Data

(63) Continuation of application No. 10/942,314, filed on Sep. 15, 2004, now Pat. No. 7,183,268, which is a continuation of application No. PCT/US03/07909, filed on Mar. 13, 2003.

(60) Provisional application No. 60/364,495, filed on Mar. 15, 2002.

(51) Int. Cl.
*C07D 473/00*    (2006.01)
*C07F 9/6561*    (2006.01)

(52) U.S. Cl.
CPC .......... *C07D 473/00* (2013.01); *C07F 9/65616* (2013.01)

(58) Field of Classification Search
None
See application file for complete search history.

(56) References Cited

U.S. PATENT DOCUMENTS 6,352,991 B1    3/2002    Zemlicka et al.
2005/0113393 A1    5/2005    Zemlicka et al.

OTHER PUBLICATIONS

Kumar, *Current Medicinal Chemistry*, 5-(1-Substituted) Alkyl Pyrimidine Nucleosides as Antiviral (herpes) Agents, 2004, 11(20), 2749-2766.
Chen, et al., *J. Med. Chem.*, Structure-Activity Relationships of (S,2)-2-Aminopurine Methylenecyclopropane Analogues of Nucleosides, Variation of Purine-6 Substituents and Activity against Herpesviruses and Hepatitis B Virus, 2003, 46, 1531-1537.
Zemlicka, et al., Frontiers in Nucleoside and Nucleic Acids, "Methylenecyclopropane analogs of nucleotides as antiviral agents," (Schinazi and Liotta, eds), IHL Press 2004, 267-307.
Qui, et al., *J. Med. Chem.*, "(Z)- and (E)-2-((Hydroxymethyl) cyclopropylidene) methyladenine and—guanine. New Nucleoside Analogues with a Broad-Spectrum Antiviral Activity" 1998, 41, 10-23.
Rybak, et al., *Antiviral Research*, "Effective treatment of murine cytomegalovirus infections with methylenecyclopropane analogues of nucleosides," 1999, 43, 165-178.
Kushner, M. L. et al., "Efficacy of Methylenecyclopropane Analogs of Nucleosides Against Herpesvirus Replication In Vitro", *Nucleosides, Nucleotides & Nucleic Acids* 2003, 22(12), 2105-2119.
Zemlicka, J., "Methylenecyclopropane Analogues of Nucleosides as Anti-Herpes Agents", *Advances in Antiviral Drug Design* 2007, 5, 113-165.
Mitsuya, H et al., "3'-Azido-3'-deoxythymidine (BW A509U): An antiviral agent that inhibits the infectivity and cytopathic effect of human T-lymphotropic virus type III/lymphadenopathy-associated virus in vitro", *Proc. Natl. Acad. Sci. USA* 1985, 82, 7096-7100.
Schaeffer, H. J. et al., "9-(2-Hydroxyethoxymethyl)guanine activity against viruses of the herpes group", *Nature* 1978, 272, 583-585.
Innaimo, S. F. et al., "Identification of BMS-200475 as a Potent and Selective Inhibitor of Hepatitis B Virus", *Antimicrobial Agents and Chemotherapy* 1997, 1444-1448.

*Primary Examiner* — Noble Jarrell
(74) *Attorney, Agent, or Firm* — Yankwich & Associates, P.C.; Leon R. Yankwich; Michael R. Wesolowski (57) ABSTRACT

Compounds which are active against viruses have the following Formulas:

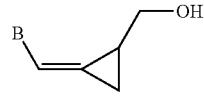

Formula 1

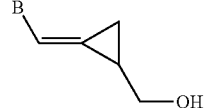

Formula 2 wherein B is 2-aminopurine-9-yl, which may be unsubstituted or substituted in the 6 position with $NHR_1$, $OR_2$, or $SR_3$;
$R_1$ is selected from the group consisting of alkyl, alkenyl, alkynyl, and $C_{4-18}$ cycloalkyl, any of which may be optionally substituted with one or more members of the group consisting of hydroxy, halo, amino, acyl, cycloalkyl, heterocyclyl and aryl;
$R_2$ is selected from the group consisting of $C_{2-18}$ alkyl, alkenyl, alkynyl, and cycloalkyl, any of which may be branched or unbranched and optionally substituted with one or more members of the group consisting of hydroxy, halo, amino, acyl, cycloalkyl, heterocyclyl, and aryl; and
$R_3$ is selected from the group consisting of alkyl, alkenyl, alkynyl, and cycloalkyl, any of which may be branched or unbranched and optionally substituted with one or more members of the group consisting of hydroxy, halo, amino, acyl, cycloalkyl, heterocyclyl and aryl.

19 Claims, 2 Drawing Sheets

2-AMINO-9-[(2-HYDROXYMETHYL) CYCLOPROPYLIDENEMETHYL] PURINES AS ANTIVIRAL AGENTS

RELATED APPLICATIONS

This application is a continuation of U.S. patent application Ser. No. 10/942,314, filed Sep. 15, 2004, now U.S. Pat. No. 7,183,268, issued Feb. 27, 2007, which is a continuation of International Application No. PCT/US03/007909, filed Mar. 13, 2003, which claims the benefit of Provisional Application No. 60/364,495, filed Mar. 15, 2002, both of which are incorporated herein by reference.

SPONSORSHIP

Work on this invention was supported in part by the National Institute of Allergy and Infectious Diseases, Grant Nos. U19-AI31718 and P01-AI46390. The Government has certain rights in the invention.

FIELD OF THE INVENTION

The present invention relates generally to novel 2-aminopurines having antiviral activity and methods for making and using them.

BACKGROUND OF THE INVENTION

Viruses are the etiologic cause of many life-threatening human diseases. Of special importance are herpes viruses such as herpes simplex 1 (HSV-1), herpes simplex 2 (HSV-2), cytomegalovirus (CMV), Epstein-Barr virus (EBV), varicella zoster virus (VZV) and human herpes viruses 6, 7 and 8 (HHV-6, -7 and -8) which are associated with many common viral illnesses. The HSV-1 and HSV-2 infections are characterized by cold sores of skin, mouth or genital region. After primary infection, the virus is harbored in neural cells and can reappear later in the life of a patient. Human CMV (HCMV) infection is a life-long affliction which can result in morbidity and mortality. These pathologies include microcephaly, hepatosplenomegaly, jaundice, encephalitis, infections of the newborn infants or fetuses in utero, and infections of immuno-compromised hosts. HCMV infection is responsible for retinitis, gastritis and pneumonitis in AIDS patients and HCMV-induced pneumonias or hepatitis are frequent and serious complications of organ or bone marrow transplants. EBV causes infectious mononucleosis and it is considered as the etiologic agent of nasopharyngeal cancer, immunoblastic lymphoma, Burkitt's lymphoma and hairy leukoplakia. VZV causes chicken pox and shingles. Although in children the chicken pox is usually a non-fatal disease, the recurrent form of this infection, shingles, may in advanced stage lead to paralysis, convulsions and ultimately death. Again, in immunocompromised patients the infection with VZV is a serious complication. Human herpes virus 6 (HHV-6) which is commonly associated with children's rash was also identified in acquired immunodeficiency syndrome (AIDS) patients and it may be a cofactor in the pathogenesis of AIDS in hosts infected with human immunodeficiency virus (HIV). Levine, A. J. *Viruses*, Ch. 4, W. H. Freeman & Co., New York, pp. 67-85 (1992); *Human Herpesvirus Infections*, Raven Press, New York (1986); Schirmer, E. C., et al., *Proc. Natl. Acad. Sci. USA* 88:5922-5926 (1992). Human herpes virus 8 (HHV-8) was identified in patients with Kaposi sarcoma, a fatal affliction accompanying AIDS. Chang, Y., et al., *Science* 266: 1865-1869 (1994).

HIV is the underlying cause of AIDS, a world-wide epidemic with fatal consequences. According to the Joint United Nations Programme on HIV/AIDS, 40 million people are estimated to be living with HIV/AIDS at the end of 2001. During that same year, AIDS caused the deaths of an estimated 3 million people.

Hepatitis B virus (HBV) is a virus that causes chronic disease responsible for serious liver damage, including cirrhosis of the liver, cancer, organ failure and ultimately, death. It is estimated that approximately 300 million people worldwide are infected with HBV. According to the CDC, there are approximately 1.25 million Americans chronically infected with HBV. Although use of a prophylactic vaccine has reduced the incidence of new HBV infections, there continues to be a need for an effective therapeutic drug.

Various derivatives of nucleoside analogues have been found to exhibit antiviral activity. Notably, acyclovir (Zovirax) and its prodrug valacyclovir (Valtrex) are approved drugs for infections caused by HSV-1 and HSV-2. *Acyclovir Therapy for Herpesvirus Infections* (Baker, Ed.), M. Dekker, New York (1990); Against HCMV, four drugs are currently available: Ganciclovir (Cytovene), cidofovir (Vistide), antisense oligonucleotide fomivirsen (Vitravene) and foscarnet (Foscavir). However, only ganciclovir is effective orally but it requires large doses and produces potentially serious adverse effects such as bone marrow suppression. *Ganciclovir Therapy for Cytomegalovirus Infection* (Spector, S. S., Ed.), M. Dekker, New York (1991). A considerable effort went into design, synthesis and biological investigation of analogues of these drugs as well as in development of new antiviral agents. Larsson, A., et al., *Antimicrob. Agents & Chemother.* 30:598-605 (1986); Ashton, W. T., et al., *J. Med. Chem.* 31:2304-2315 (1988). Cidofovir and fomivirsen are approved only for topical application against retinitis in AIDS patients and foscarnet is used only by intravenous route and it leads to characteristic toxicity.

Current drugs for AIDS include AZT (zidovudine, Retrovir), ddI (didanosine, Videx), ddC (zalcitabine, Hivid) and d4T (stavudine, Zerit). De Clercq, E., *J. Med. Chem.* 38:2491-2517 (1995). Allenic nucleoside analogues such as adenallene and cytallene are examples of anti-HIV agents containing an unsaturated alkyl group. U.S. Pat. No. 4,935,427; Zemlicka, J., *Allenols Derived from Nucleic Acid Bases—a New Class of Anti-HIV Agents: Chemistry and Biological Activity in Nucleosides and Nucleotides as Antitumor and Antiviral Agents* (Chu, C. K.; Baker, D. C., Eds.), Plenum Press, New York, pp. 73-100 (1993). For HBV, alpha interferon and 3TC (lamivudine; Epivir) are two drugs licensed for the treatment of persons with chronic HBV infection. Unfortunately, only about 40% of patients respond to these drugs and resistance is a growing problem.

Particular 2-hydroxymethylcyclopropylidenemethylpurines and their utility against certain viruses have been described elsewhere (see, for example, co-owned U.S. Pat. No. 6,352,991; Qiu, Y. L., et al., *J. Med. Chem.* 41:10-23 (1998); *Antiviral Chem. Chemother.* 9:341-352 (1998)). However, there continues to be a need for novel compounds which are active against pathogenic viruses, including HCMV, HSV-1, HSV-2, HHV-6, HIV, and hepatitis B virus (HBV).

SUMMARY OF THE INVENTION

The present invention provides novel 2-amino-9-[(2-hydroxymethyl)cyclo-propylidenemethyl]purines, including all geometric and optically active isomers, prodrugs and pharmacologically acceptable salts thereof. These compounds have been found to be useful antiviral agents and are effective against HCMV, HSV-1, HSV-2, HHV-6, HIV, EBV and HBV, as well as against other pathogenic viruses.

The compounds of the present invention have the following Formulas:

Formula 1

Formula 2 wherein B is 2-aminopurine-9-yl, which may be unsubstituted or substituted in the 6 position with $NHR_1$, $OR_2$, or $SR_3$;

$R_1$ is selected from the group consisting of alkyl, alkenyl, alkynyl, and $C_{4-18}$ cycloalkyl, any of which may be optionally substituted with one or more members of the group consisting of hydroxy, halo, amino, acyl, cycloalkyl, heterocyclyl and aryl;

$R_2$ is selected from the group consisting of $C_{2-18}$ alkyl, alkenyl, alkynyl, and cycloalkyl, any of which may be branched or unbranched and optionally substituted with one or more members of the group consisting of hydroxy, halo, amino, acyl, cycloalkyl, heterocyclyl, and aryl; and $R_3$ is selected from the group consisting of alkyl, alkenyl, alkynyl, and cycloalkyl, any of which may be branched or unbranched and optionally substituted with one or more members of the group consisting of hydroxy, halo, amino, acyl, cycloalkyl, heterocyclyl and aryl.

The compounds of the present invention also include, including all geometric and optically active isomers, prodrugs and pharmacologically acceptable salts of the novel 2-amino-9-[(2-hydroxymethyl)cyclopropylidene-methyl] purine compounds of this invention.

Compositions of this invention useful for treating viral infections, such as HCMV, HSV-1, HSV-2, HHV-6, HIV, EBV and HBV, comprise an effective amount of at least one compound according to this invention or a pharmaceutically acceptable salt thereof and a pharmaceutically acceptable carrier.

Additional objects, advantages, and features of the present invention will become apparent from the description that follows.

DETAILED DESCRIPTION OF THE PREFERRED EMBODIMENTS

As used herein, the following terms shall be defined as follows (unless otherwise noted):

"Acyl" shall mean the radical C(O)R, wherein R is selected from alkyl, aryl, alkylaryl, arylakyl (such as benzyl), alkylarylalkyl, heterocyclyl, heterocyclylalkyl, carbocyclyl, carbocyclylalkyl, alkoxyalkyl (such as methoxymethyl), alkoxyalkyl, aryloxyalkyl (such as phenoxymethyl), poly (alkyloxy)alkyl (such as polyethers like poly (methoxy)methyl), aryl (such as phenyl optionally substituted with halo, lower alkyl or lower alkoxy), arylalky, and alkylaryl. Specific examples of acyl moieties include, without limitation, acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic and oleaoic.

"Alkyl" shall mean a saturated straight chain or branched, primary, secondary, or tertiary hydrocarbon radical that is fully saturated, typically $C_1$-$C_{18}$, preferably $C_1$-$C_{10}$, and more preferably $C_1$-$C_6$ Preferred alkyl groups include, without limitation, methyl, ethyl, propyl, butyl, pentyl, hexyl, isopropyl, isobutyl, sec-butyl, t-butyl, isopentyl, amyl, and t-pentyl. In the case of $R_2$, preferred alkyl groups are $C_2$-$C_{18}$, preferably $C_2$-$C_{10}$, and more preferably $C_2$-$C_6$, and include, without limitation, ethyl, propyl, butyl, pentyl, hexyl, isopropyl, isobutyl, sec-butyl, t-butyl, isopentyl, amyl, and t-pentyl.

"Alkenyl" shall mean an alkyl moiety having at least one double bond. Alkenyl groups containing three or more carbon atoms may be straight or branched.

"Alkynyl" shall mean an alkyl moiety having at least one triple bond. Alkynyl groups containing three or more carbon atoms may be straight or branched.

"Amino acid" shall mean an amino acid or amino acid residue selected from the group of all of the naturally occurring amino acids, those amino acids in their D- and L-configurations, and the known non-native, synthetic, and modified amino acids, such as homocysteine, ornithine, norleucine and .beta.-valine. A list of non natural amino acids may be found in "The Peptides", vol 5, 1983, Academic Press, Chapter 6 by D. C. Roberts and F. Vellaccio. In the context of the substituents $R_1X$ or $R_2X$ in Formulas 3 and 4, preferred amino acid residues include alanine and tryptophan.

"Aryl" shall mean a mono- or polycyclic aromatic ring or ring system which may be carbocyclic or heterocyclic and may be unsubstituted or substituted with one or more substituents selected from (but not limited to) alkyl (preferably, lower alkyl), hydroxy, alkoxy (preferably, lower alkoxy), alkylthio, cyano, halo, amino, and nitro). Examples of aryl groups are phenyl, methylphenyl, dimethylphenyl, aminophenyl, nitrophenyl, hydroxyphenyl, and the like.

"Cycloalkyl" shall mean a mono-, bi- or polycyclic alkyl radical. For convenience, the term "cycloalkyl" shall also expressly include cycloalkenyl cycloalkynyl radicals. A "branched cycloalkyl" shall mean a cycloalkyl ring in which one or more ring members are substituted with alkyl. In general, these rings shall typically be $C_3$-$C_{18}$, preferably $C_3$-$C_{10}$, and more preferably $C_3$-$C_8$. In the case of $R_1$, the cycloalkyl radical is preferably $C_4$-$C_{18}$, more preferably, $C_4$-$C_{12}$ and most preferably, $C_4$-$C_{10}$.

"Halo" shall mean fluoro, chloro, bromo, or iodo.

"Heterocyclyl" shall mean a mono-, bi- or polycyclic radical containing one or more rings which may be saturated, unsaturated, or aromatic, wherein at least one ring contains one or more heteroatoms selected from nitrogen (N), oxygen (O), and sulfur (S). Heterocyclyl radicals typically have 3-18 total ring members and preferably 3-10 total ring members. Preferably, heterocyclyl radicals are monocyclic (preferably having 3-8 and more preferably, 3-6 ring members) or bicyclic (preferably having 6-12 ring members and more preferably, 8-10 ring members). Suitable heterocyclyl for use in the compounds of this invention include radicals of (without limitation) furan, dioxolane, thiophene, pyrrole, pyrazole, triazole, imidazole, pyrrolidine, pyran, pyridine, pyrimidine, morpholine, piperidine, oxazole, isoxazole, oxazoline, oxazolidine, oxathiazole, thiazole, isothiazole, thiadiazole, tetrazole, benzofuran, indole, isoindole, quinazoline, quinoline, isoquinoline, purine, pyrrolopyrimidine, pyrrazolopyrimidine, pteridine, ketal. In addition, heterocyclyl radicals may contain one or more substituents (i.e., a ring substituent, such as a halogen atom, an alkyl radical, or aryl radical) attached to a ring member atom of the heterocyclyl radical. All stable isomers of heterocyclyl groups are contemplated in this definition.

"Lower" shall mean the group to which it is applied preferably has 1-6, and more preferably 1-4, carbon atoms, except in the case of rings (such as cycloalkyl and heterocyclyl), in which case "lower" signifies 3-6 ring members.

"Patient" shall mean any warm-blooded mammal, including without limitation, a human.

"Pharmaceutically acceptable salts" shall mean those salts of any compound of this invention derived from an inorganic or organic acid or base recognized in the art as compatible for pharmaceutical compositions. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal (e.g., sodium, potassium), alkaline earth metal (e.g., magnesium), ammonium and $NR_4^+$ (where R is a $C_{1-4}$ alkyl) salts, and the like. Reference to a compound according to the invention is understood to include any and all corresponding pharmaceutically acceptable salts thereof. For convenience, the terms "pharmaceutical" and "pharmaceutically acceptable" are understood to encompass compounds acceptable for the practice of veterinary medicine as well.

"Pharmaceutically acceptable carriers" for use in the formulations of this invention are carriers that are compatible with the other ingredients of the formulation and not deleterious to the recipient thereof.

""Therapy" and "therapeutic" shall mean treatment of an individual for a viral infection or disease. For convenience, these terms are also understood to encompass prophylactic or precautionary use or administration of a compound of this invention. Such precautionary or prophylactic use is exemplified by administration of an antiviral agent to an individual(s) suspected, but not proven, of having a viral infection or to an individual(s) susceptible to contracting a pathogenic viral infection due to contact with contaminated items, or contact with other individuals carrying a contagious viral disease.

All published documents referred to herein are expressly incorporated herein by reference.

The compounds of the present invention which have been found to be effective against pathogenic viruses including HCMV, HSV-1, HSV-2, HHV-6, HIV, EBV and HBV, are compounds of Formulas 1 and 2:

Formula 1

Formula 2 wherein B is 2-aminopurine-9-yl, which may be unsubstituted or substituted in the 6 position with $NHR_1$, $OR_2$, or $SR_3$;

$R_1$ is selected from the group consisting of alkyl, alkenyl, alkynyl, and $C_{4-18}$ cycloalkyl, any of which may be optionally substituted with one or more members of the group consisting of hydroxy, halo, amino, acyl, cycloalkyl, heterocyclyl and aryl;

$R_2$ is selected from the group consisting of $C_{2-18}$ alkyl, alkenyl, alkynyl, and cycloalkyl, any of which may be branched or unbranched and optionally substituted with one or more members of the group consisting of hydroxy, halo, amino, acyl, cycloalkyl, heterocyclyl, and aryl; and $R_3$ is selected from the group consisting of alkyl, alkenyl, alkynyl, and cycloalkyl, any of which may be branched or unbranched and optionally substituted with one or more members of the group consisting of hydroxy, halo, amino, acyl, cycloalkyl, heterocyclyl and aryl.

In a preferred embodiment, B is 2-aminopurine-9-yl, which is substituted in the 6 position with $NHR_1$, $OR_2$, or $SR_3$; wherein $R_1$ is selected from the group consisting of $C_1$-$C_8$ alkyl, $C_3$-$C_8$ alkenyl, $C_3$-$C_8$ alkynyl, and $C_{4-10}$ cycloalkyl, any of which may be optionally substituted with one or more members of the group consisting of hydroxy, halo, amino, acyl, cycloalkyl, heterocyclyl and aryl;

$R_2$ is selected from the group consisting of $C_{2-8}$ alkyl, $C_3$-$C_8$ alkenyl, $C_3$-$C_8$ alkynyl, and $C_{3-10}$ cycloalkyl, any of which may be branched or unbranched and optionally substituted with one or more members of the group consisting of hydroxy, halo, amino, acyl, cycloalkyl, heterocyclyl, and aryl; and $R_3$ is selected from the group consisting of $C_{2-8}$ alkyl, $C_3$-$C_8$ alkenyl, $C_3$-$C_8$ alkynyl, and $C_{3-10}$ cycloalkyl, any of which may be branched or unbranched and optionally substituted with one or more members of the group consisting of hydroxy, halo, amino, acyl, cycloalkyl, heterocyclyl and aryl.

In another preferred embodiment, B is 2-aminopurine-9-yl, which is substituted in the 6 position with $NHR_1$, $OR_2$, or $SR_3$; wherein $R_1$ is selected from the group consisting of $C_1$-$C_6$ alkyl, $C_3$-$C_6$ alkenyl, $C_3$-$C_6$ alkynyl, and $C_{4-8}$ cycloalkyl, any of which may be optionally substituted with one or more members of the group consisting cycloalkyl, heterocyclyl and aryl;

$R_2$ is selected from the group consisting of $C_{2-6}$ alkyl, $C_3$-$C_6$ alkenyl, $C_3$-$C_6$ alkynyl, and $C_{3-8}$ cycloalkyl, any of which may be branched or unbranched and optionally substituted with one or more members of the group consisting of cycloalkyl, heterocyclyl, and aryl; and $R_3$ is selected from the group consisting of $C_{2-6}$ alkyl, $C_3$-$C_6$ alkenyl, $C_3$-$C_6$ alkynyl, and $C_{3-8}$ cycloalkyl, any of which may be branched or unbranched and optionally substituted with one or more members of the group consisting of hydroxy, halo, amino, acyl, cycloalkyl, heterocyclyl and aryl.

Preferred compounds of the present invention are:

(Z,S)-(+)-2-Amino-6-allylamino-9-[(2-hydroxymethyl)cy-clopropylidene-methyl]purine;
(Z,S)-(+)-2-Amino-6-propargylamino-9-[(2-hydroxymethyl)cyclo-propylidenemethyl]purine;
(Z,S)-(+)-2-Amino-6-cyclopropylmethylamino-9-[(2-hydroxymethyl)-cyclopropylidenemethyl]purine;
(Z,S)-(+)-2-Amino-6-isopropylamino-9-[(2-hydroxymethyl)cyclopropylidenemethyl]purine;
(Z,S)-(+)-2-Amino-6-benzylamino-9-[(2-hydroxymethyl)cyclopropylidenemethyl]purine;
(Z,S)-(+)-2-Amino-6-cyclohexylamino-9-[(2-hydroxymethyl)cyclopropylidenemethyl]purine;
(Z,S)-(+)-2-Amino-6-(2-hydroxy)ethylamino-9-[(2-hydroxymethyl)cyclopropylidenemethyl]purine;
(Z,S)-(+)-2-Amino-6-propoxy-9-[(2-hydroxymethyl)cyclopropylidenemethyl]purine;
(Z,S)-(+)-2-Amino-6-pentyloxy-9-[(2-hydroxymethyl)cyclopropylidenemethyl]purine;
(Z,S)-(+)-2-Amino-6-allyloxy-9-[(2-hydroxymethyl)cyclopropylidenemethyl]purine;
(Z,S)-(+)-2-Amino-6-cyclopropylmethoxy-9-[(2-hydroxymethyl)cyclopropylidenemethyl]purine;
(Z,S)-(+)-2-Amino-6-propylthio-9-[(2-hydroxymethyl)cyclopropylidenemethyl]purine;
(Z,S)-(+)-2-Amino-6-pentylthio-9-[(2-hydroxymethyl)cyclopropylidenemethyl]purine;
(Z,S)-(+)-2-Amino-6-thio-9-[(2-hydroxymethyl)cyclopropylidenemethyl]purine; and
(Z,S)-(+)-2-Amino-9-[(2-hydroxymethyl)cyclopropylidenemethyl]purine.

Prodrugs of the antiviral compounds of the present invention include lipophilic phosphate esters or amidates capable of penetrating the cell membrane. Those skilled in the art will appreciate that the aim of prodrugs is to provide effective therapeutic agents for resistant strains of viruses (McGuigan, C., et al., *J. Med. Chem.* 36:1048-1052 (1993)) or activate inactive analogs (Franchetti, P., et al., *J. Med. Chem.* 37:3534-3541 (1994)). Preferred prodrugs include the phosphate esters of Formulas 3 and 4:

Formula 3

Formula 4 wherein
B is defined as above for Formulas 1 and 2;
X is O; and
$R_1$ and $R_2$ are alkyl or aryl. The $R_1X$ or $R_2X$ may also be amino acid residues (such as alanine) with X as NH.

The nomenclature of the compounds of the present invention follows standard conventions. For the sake of clarity, the purine ring B is numbered according to the standard convention as indicated below:

It is appreciated that heterocyclic rings containing hydroxy and amino groups are tautomeric with the corresponding oxo and imino compounds.

The compounds described by Formulas 1 through 4 contain an asymmetric carbon atom. Compounds of Formula 1 and 2 of the present invention are therefore racemic mixtures of two optical antipodes which may be resolved by conventional methods such as chromatography or fractional crystallization of suitable diastereoisomeric derivatives such as salts or esters with optically active acids (camphor 10-sulfonic acid, methoxyacetic acid, dibenzoyltartaric acid, 6-methoxy-2-naphthyl-2-propanoic acid, etc.), by an enantioselective enzymic synthesis of esters of one antipode such as acetates or butyrates or by an enantioselective enzymic hydrolysis of esters of compounds of Formulas 1 and 2, such as acetates or butyrates. The suitable enzymes include, but are not limited to, lipases such as lipase AK, lipase P30 or esterases such as pig liver esterase. Racemic compounds containing adenine moiety may also be resolved by the action of adenosine deaminase. Alternatively, the R- and S-enantiomers can be obtained by synthetic methods utilizing enantiomerically pure starting materials. The compounds of this invention expressly include the racemic mixture and the individual optically isomers (e.g., R- and S-enantiomers) of each of these compounds, their pharmaceutically acceptable salts and prodrugs thereof. Preferred compounds of the present invention include the individual R- and S-enantiomers of the compounds of Formulas 1-4 and more preferably, the R- and S-enantiomers of the compounds of Formulas 1 and 2.

Compounds of formulas 3 and 4 derived from racemic analogues of compounds of Formulas 1 and 2 will be mixtures of four diastereoisomers (provided that $R_1X$ is not the same as $R_2X$).

Figure 1:
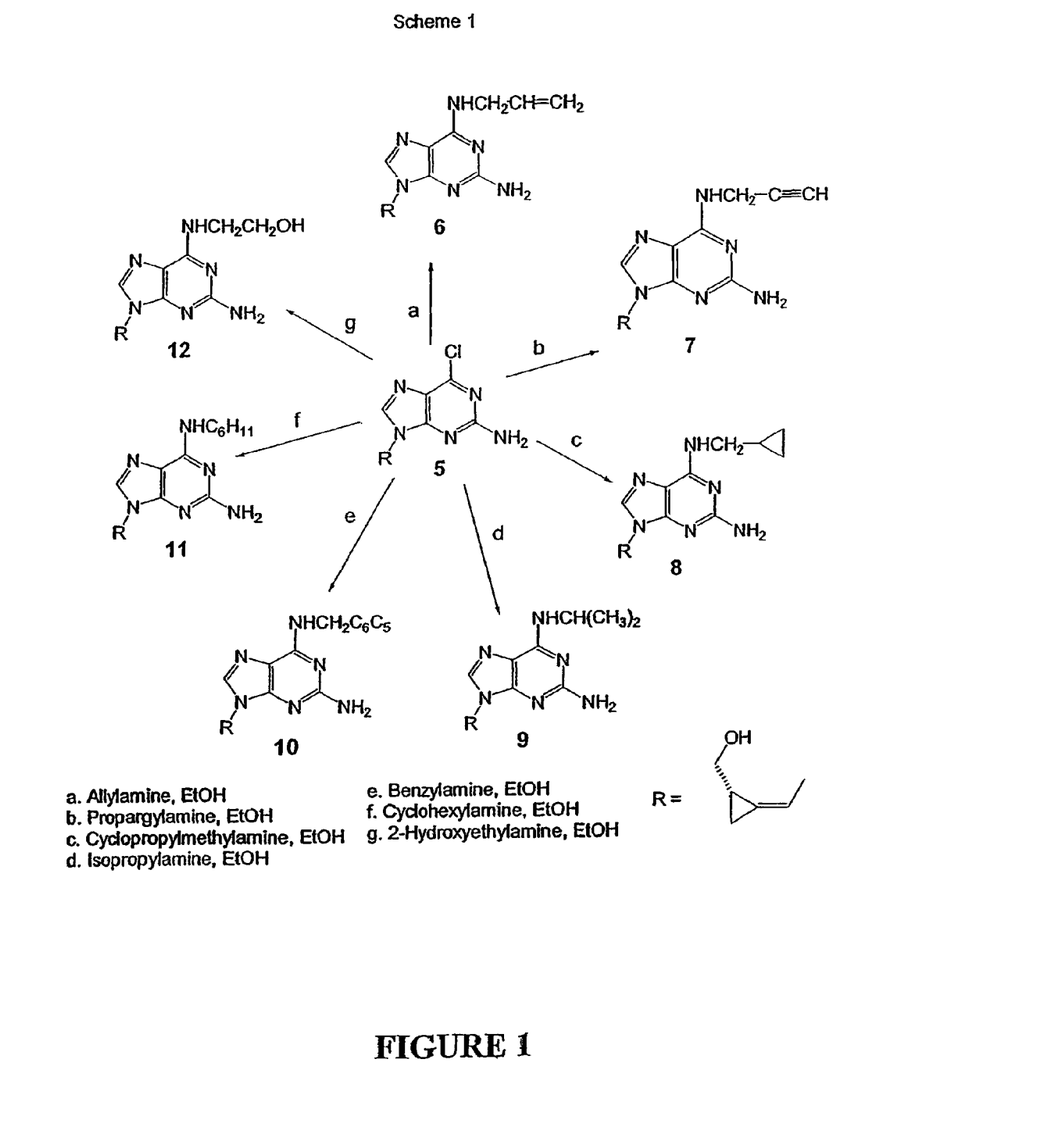
FIG. 1 depicts Scheme 1 which illustrates the synthesis of some compounds of the present invention.
Figure 2:
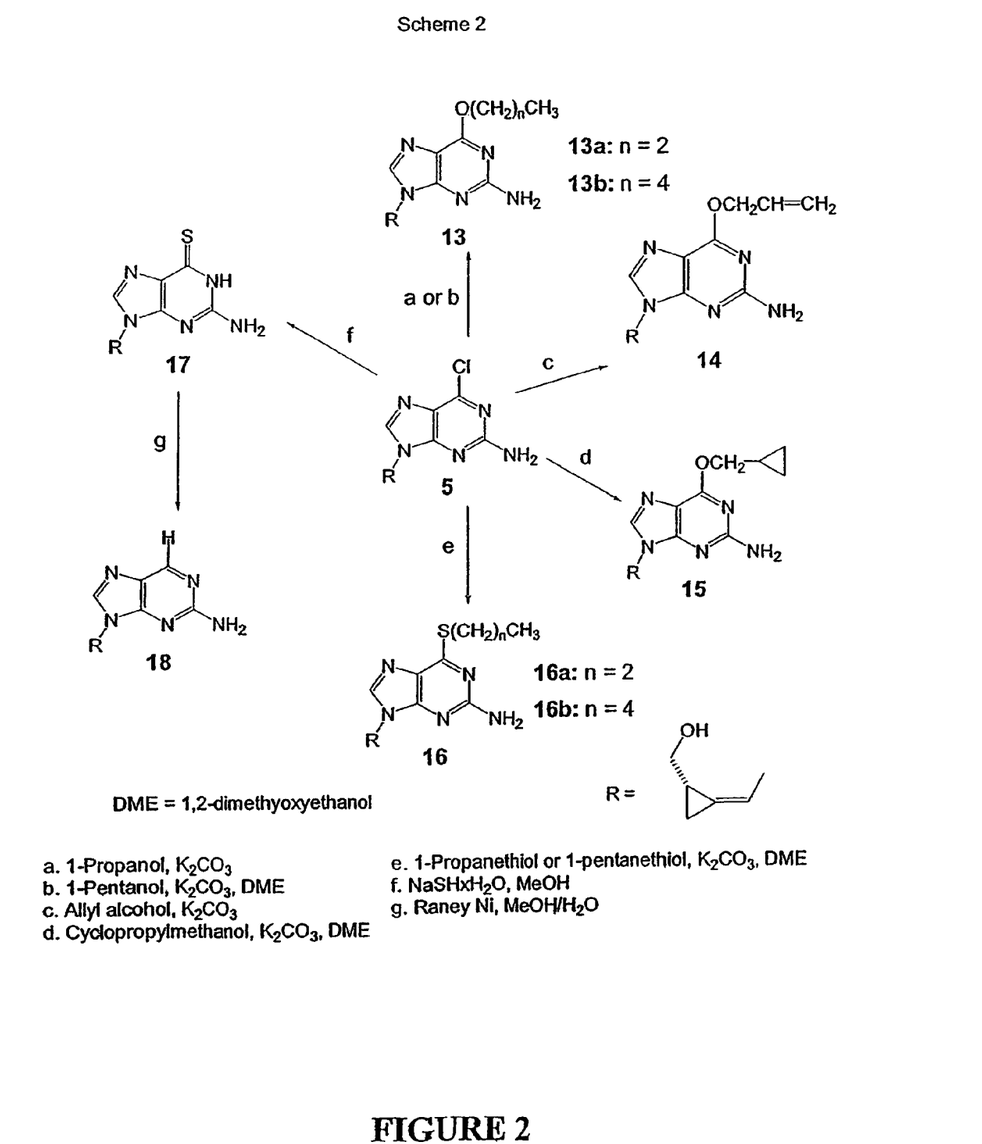
FIG. 2 depicts Scheme 2 which illustrates the synthesis of some compounds of the present invention.

In Schemes 1 and 2 attached hereto, (Z)-2-amino-6-chloro-9-[(2-hydroxymethyl)cyclopropylidenemethyl]purine (Compound 5, see Scheme 1) is used as a convenient starting material for compounds of this invention. This compound can be obtained in racemic or enantiomeric (R or S') form along with the corresponding E-isomer (Qiu et al., *J. Med. Chem.* 1998, 41, 10-23; Qiu and Zemlicka, *Synthesis* 1998 11447-1452; Qiu et al., *Antiviral Chem. Chemother.* 2000, 11 191-202; Chen and Zemlicka, *J. Org. Chem.* 2002, 67, 286-289). For purpose of illustration, the S-enantiomer is shown in Compound 5). The reactivity of the chlorine atom of Compound 5 provides for easy substitution with amines, as shown, for example, in Scheme 1 (Compounds 6-12). Such substitution may be conducted (for example) with alcohols (Scheme 2, Compounds 13a-15), thiols (Scheme 2, Compounds 16a and 16b), and sodium hydroxulfide (Scheme 2, Compound 17). Reduction of Compound 17 gives the 6-unsubstituted 2-aminopurine derivative, Compound 18. These procedures can be readily modified by those of ordinary skill in the art to produce other examples of compounds of this invention. For example, this procedure may be used with the E-isomer of Compound 5.

Compositions within the scope of invention include those comprising a novel compound of the present invention in an effective amount to achieve an intended purpose, such as antiviral efficacy. Determination of an effective amount and intended purpose is within the skill of the art. Preferred dosages, which are dependent for example, on the severity of the infection and the individual patient's response to the treatment, can range from about 0.01 to about 100 mg/kg of body weight per day (preferably in the range of 0.5 to 60 mg/kg/day, most preferably in the range of 1 to 20 mg/kg/day) to give a blood concentration ranging from about 0.05 Φg to about 5 mg per mL of whole blood (preferably, 1 to about 75 µM, more preferably about 2 to 50 µM, most preferably about 3 to about 30 µM).

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutically acceptable compositions of the present invention may include suitable carriers comprising excipients and auxiliaries which facilitate processing of the active compounds into preparations which may be used pharmaceutically. Such preparations, preferably those which can be administered orally, include tablets, dragees, liquids, caplets, and capsules. Further preferred preparations are those which can be administered vaginally or rectally, such as suppositories, as well as suitable solutions for administration by injection or orally, contain from about 0.1 to about 99%, preferably about 25 to about 85%, of the active compound of the present invention, together with the excipient.

The pharmaceutical compositions of the present invention are manufactured in a manner which is itself known, e.g. using the conventional mixing, granulating, dragee-making, dissolving or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, e.g., lactose or sucrose, mannitol or sorbitol, cellulose preparations and/or calcium phosphates, e.g., tricalcium diphosphate or calcium hydrogen phosphate, as well as binders such as starch paste, using, e.g., maize starch, wheat starch, rice starch, potato starch, gelatin, gum tragacanth, methyl cellulose and/or polyvinylpyrrolidone. If desired, disintegrating agents may be added such as the above-mentioned starches and also carboxymethyl starch, cross-linked polyvinylpyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvent or solvent mixtures. In order to produce coatings resistant to gastric juices, solutions of suitable cellulose preparations, such as acetylcellulose phthalate or hydroxypropylmethylcellulose phthalate, are used. Dyestuffs or pigments may be added to the tablets or dragee coatings, e.g., for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be used.

Possible pharmaceutical preparations which can be used rectally include, e.g., suppositories, which consist of a combination of the active compounds with a suppository base. Suitable suppository bases are, e.g., natural or synthetic triglycerides, paraffin hydrocarbons, polyethylene glycols or higher alkanols. It is also possible to use gelatin rectal capsules which consist of a combination of the active compounds with a base. Possible base materials include, e.g., liquid triglycerides, polyethylene glycols or paraffin hydrocarbons.

Suitable formulations for parenteral administration include aqueous solutions of the active compounds in water-soluble form, e.g., water-soluble salts. In addition, suspension of the active compounds as appropriate oily injection suspensions may be administered. Suitable lipophilic solvents or vehicles include fatty oils, such as sesame oil, or synthetic fatty acid esters, e.g., ethyl oleate or triglycerides. Aqueous injection suspensions may contain substances which increase the viscosity of the suspension such as sodium carboxymethylcellulose, sorbitol and/or dextran. Optionally, the suspension may also contain stabilizers.

When desired, the above described formulations may be adapted to give a sustained or time-delayed release of compound of the invention using any of the sustained or time-delayed formats available in art.

Alternatively, the active compounds of the present invention may be administered in the form of liposomes, pharmaceutical compositions wherein the active compound is contained either dispersed or variously present in corpuscles consisting of aqueous concentrate layers adherent to hydrophobic lipidic layer. The active compound may be present both in the aqueous layer and in the lipidic layer or in the non-homogeneous system generally known as a lipophilic suspension.

It will be appreciated that the active compounds of the present invention may be administered in combination with other therapeutic agents, including known antiviral agents, e.g., acyclovir, ganciclovir, zidovudine, AZT, ddI, ddC, 3TC and d4T. The individual components of such combinations may be administered either sequentially or simultaneously in separate or combined pharmaceutical formulations. When a compound of the invention or a pharmaceutically acceptable salt thereof is used in combination with a second therapeutic compound, the dose of each compound may be either the same as or differ from that when the compound is used alone. Appropriate doses will be readily appreciated by those skilled in the art.

The ratio between a compound of the present invention and a second therapeutic agent will be readily appreciated by those skilled in the art. For example, one may use a ratio in the range from about 1:1 to about 1:50 (by weight) of compound of the invention:second therapeutic agent. In a further embodiment, one may use a ratio ranging from about 1:1 to about 1:30 (by weight) of a compound of the invention:second therapeutic agent. In a further embodiment, one may use a ratio from about 1:1 to about 1:20 (by weight) of a compound of the invention:second therapeutic agent. In a further embodiment, one may use a ratio in the range from about 1:1 to about 1:15 (by weight) of a compound of the invention: second therapeutic agent. In a further embodiment, one may use a ratio ranging from about 1:1 to about 1:10 (by weight) of a compound of the invention:second therapeutic agent. In a further embodiment, one may use a ratio in the range from about 1:1 to about 1:5 (by weight) of a compound of the invention:second therapeutic agent. In yet a further embodiment, one may use a ratio in the range of about 1:1 to about 1:3 (by weight) of a compound of the invention:second therapeutic agent. If more than one additional therapeutic agent is used in combination with a compound of this invention, the above ratios may be adjusted accordingly.

EXAMPLES

The following Examples further describe the compounds of the present invention and the synthesis schemes for producing same (reference should be made to Schemes 1 and 2 above for compound numbers). These Examples are provided to illustrate various embodiments of the present invention and shall not be considered as limiting in scope.

Compound 5 was prepared as described (Chen, X.; Zemlicka, J. J. Org. Chem. 2002, 67, 286-289).

Example 1

(Z,S)-(+)-2-Amino-6-allylamino-9-[(2-hydroxymethyl)cyclopropylidenemethyl]purine (6)

A mixture of compound 5 (503 mg, 2.0 mmol) and allylamine (680 mg, 12 mmol) in ethanol (20 mL) was stirred overnight at room temperature. Volatile components were evaporated in vacuo and the residue was chromatographed on a silica gel column using dichloromethane-methanol (95:5) to give product 6 (445 mg, 82%).

Mp. 168-170° C. $[\alpha]^{20}_D$ 70.2° (c=0.45, N,N-dimethylformamide). $^1$H NMR (DMSO-$d_6$, 500 MHz) δ 1.14-1.17 (m, 1H), 1.42-1.46 (m, 1H), 2.06-2.09 (m, 1H), 3.30-3.35 (m, 1H), 3.66-3.70 (m, 1H). 4.04 (bs, 2H), 5.00-5.14 (m, 1H), 5.88-5.95 (m, 1H), 5.97 (bs, 2H), 7.17 (d, 1H, J=1.5 Hz), 7.48 (bs, 1H), 8.33 (s, 1H). $^{13}$C NMR (DMSO-$d_6$, 125 MHz) ppm 6.9, 19.8, 42.4, 63.7, 111.0, 114.2, 115.4, 134.7, 136.8, 150.4, 155.4, 161.2. ESI-MS (NaCl+KCl) 567 (2M+Na, 60), 311 (M+K, 15), 295 (M+Na, 58), 273 (M+H, 100). Calculated for $C_{13}H_{16}N_6O$: C, 57.34; H, 5.92; N, 30.86. Found: C, 57.32; H, 5.82; N, 30.91.

Example 2

(Z,S)-(+)-2-Amino-6-propargylamino-9-[(2-hydroxymethyl)-cyclopropylidenemethyl]purine (7)

A mixture of compound 5 (190 mg, 0.75 mmol) and propargylamine (270 mg, 4.8 mmol) in ethanol (18 mL) was stirred at 50° C. for 1 h and the stirring was continued for 16 h at room temperature. The work-up followed the procedure described in Example 1 to give compound 7 (175 mg, 85%).

Mp. 192-194° C. $[\alpha]^{20}_D$ 77.3° (c=0.40, N,N-dimethylformamide). $^1$H NMR (DMSO-$d_6$, 500 MHz) δ 1.15-1.18 (m, 1H), 1.43-1.47 (m, 1H), 2.03-2.14 (m, 1H), 3.03 (s, 1H), 3.29-3.35 (m, 1H), 3.67 (m, 1H), 4.19 (d, 2H, J=3.2 Hz), 5.07 (t, 1H, J=5.0 Hz), 6.08 (bs, 2H), 7.18 (d, 1H, J=2.5 Hz), 7.69 (bs, 1H), 8.36 (s, 1H). $^{13}$C NMR (DMSO-$d_6$, 100 MHz) ppm 6.9, 19.8, 29.3, 63.7, 73.1, 83.0, 110.9, 113.6, 114.4, 135.1, 154.8, 161.1. ESI-MS (NaCl) 563 (2M+Na, 80), 293 (M+Na, 100.0), 271 (M+H, 18). Calculated for $C_{13}H_{14}N_6O$: C, 57.77; H, 5.22; N, 31.09. Found: C, 57.81; H, 5.39; N, 31.11.

Example 3

(Z,S)-(+)-2-Amino-6-cyclopropylmethylamino-9-[(2-hydroxymethyl)cyclopropylidenemethyl]purine (8)

A mixture of compound 5 (200 mg, 0.8 mmol) and cyclopropylmethylamine (360 mg, 5.0 mmol) in ethanol (15 mL) was stirred at 50° C. for 16 h. The work-up followed the procedure described in Example 1 to give compound 8 (201 mg, 88%).

Mp. 180-182° C. $[\alpha]^{20}_D$ 68.4° (c=0.28, N,N-dimethylformamide). $^1$H NMR (DMSO-$d_6$, 400 MHz) δ 1.06-1.12 (m, 1H), 1.14-1.17 (m, 1H), 1.44 (dt, 1H, J=8.4 Hz and 1.6 Hz), 2.04-2.09 (m, 1H), 3.26-3.36 (m, 3H), 3.66-3.72 (m, 1H), 5.10 (t, 1H, J=5.2 Hz), 5.97 (bs, 2H), 7.19 (s, 1H), 7.35 (bs, 1H), 8.33 (s, 1H). $^{13}$C NMR (DMSO-$d_6$, 100 MHz) ppm 4.0, 6.9, 12.0, 19.9, 44.5, 63.7, 111.1, 113.6, 114.1, 134.6, 150.3, 155.5, 161.2. ESI-MS(NaCl) 309 (M+Na, 55), 287 (M+H, 100). Calculated for $C_{14}H_{18}N_6O$: C, 58.73; H, 6.34; N, 29.35. Found: C, 58.95; H, 6.33; N, 29.43.

Example 4

(Z,S)-(+)-2-Amino-6-isopropylamino-9-[(2-hydroxymethyl)-cyclopropylidenemethyl]purine (9)

A mixture of compound 5 (250 mg, 1.0 mmol) and isopropylamine (590 mg, 10 mmol) in ethanol (10 mL) was stirred at room temperature for 16 h. The work-up followed the procedure described in Example 1 to give compound 9 (215 mg, 80%).

Mp. 153-155° C. $[\alpha]^{20}_D$ 67.8° (c=0.36, N,N-dimethylformamide). $^1$H NMR (DMSO-$d_6$, 500 MHz) δ 1.15 (d, 6H, J=6.5 Hz), 1.14-1.16 (m, 1H), 1.43 (m, 1H), 2.03-2.12 (m, 1H), 3.30-3.35 (m, 1H), 3.67-3.69 (m, 1H), 4.37 (m, 1H), 5.10 (t, 1H, J=5.0 Hz), 5.94 (bs, 2H), 7.01 (bs, 1H), 7.18 (s, 1H), 8.32 (s, 1H). $^{13}$C NMR (DMSO-$d_6$, 125 MHz) ppm 6.9, 19.8, 23.3, 41.4, 63.7, 111.1, 113.5, 114.1, 134.5, 150.3, 154.9, 161.2. ESI-MS(NaCl) 571 (2M+Na, 50), 297 (M+Na, 50), 275 (M+H, 100). Calculated for $C_{13}H_{18}N_6O$: C, 56.92; H, 6.61; N, 30.64. Found: C, 57.09; H, 6.40; N, 30.76.

Example 5

(Z,S)-(+)-2-Amino-6-benzylamino-9-[(2-hydroxymethyl)cyclopropylidenemethyl]purine (10)

A mixture of compound 5 (250 mg, 1.0 mmol) and benzylamine (645 mg, 6.0 mmol) in ethanol (15 mL) was stirred at 50° C. for 16 h. The work-up followed the procedure described in Example 1 to give after chromatography in dichloromethane-methanol (97:3) compound 10 (240 mg, 75%).

Mp. 133-135° C. $[\alpha]^{20}_D$ 69.7° (c=0.35, N,N-dimethylformamide). $^1$H NMR (DMSO-$d_6$, 400 MHz) δ 1.14-1.18 (m, 1H), 1.43-1.48 (m, 1H), 2.03-2.11 (m, 1H), 3.28-3.32 (m, 1H), 3.65-3.70 (m, 1H), 4.62 (s, 2H), 5.07 (t, 1H, J=5.0 Hz), 5.96 (bs, 2H), 7.17-7.20 (m, 2H), 7.25-7.30 (m, 4H), 7.86 (bs, 1H), 8.32 (s, 1H). $^{13}$C NMR (DMSO-$d_6$, 100 MHz) ppm 6.9, 19.9, 43.2, 63.7, 111.1, 113.6, 114.3, 127.2, 127.9, 128.8, 134.8, 141.2, 150.5, 155.5, 161.2. ESI-MS (NaCl) 345

(M+Na, 60), 323 (M+H, 100). Calculated for $C_{17}H_{18}N_6O$: C, 63.34; H, 5.63; N, 26.07. Found: C, 63.57; H, 5.67; N, 25.93.

Example 6

(Z,S)-(+)-2-Amino-6-cyclohexylamino-9-[(2-hydroxymethyl)-cyclopropylidenemethyl]purine (11)

A mixture of compound 5 (200 mg, 0.8 mmol) and cyclohexylamine (645 mg, 6.5 mmol) in ethanol (15 mL) was refluxed with stirring for 16 h. The work-up followed the procedure described in Example 5 to give compound 11 (205 mg, 82%).

Mp. 183-185° C. $[\alpha]^{20}_D$ 81.2° (c=0.34, N,N-dimethylformamide). $^1$H NMR (DMSO-$d_6$, 400 MHz) δ 1.07-1.29 (m, 6H), 1.44 (t, 1H, J=8.0 Hz), 1.56 (d, 1H, J=11.6 Hz), 1.67-1.70 (m, 2H), 1.78-1.88 (m, 2H), 2.00-2.11 (m, 1H), 3.30-3.35 (m, 1H), 3.66-3.69 (m, 1H), 4.01 (bs, 1H), 5.10 (t, 1H, J=5.2 Hz), 5.93 (bs, 2H), 6.95 (bs, 1H), 7.18 (s, 1H), 8.31 (s, 1H). $^{13}$C NMR (DMSO-$d_6$, 100 MHz) ppm 6.9, 19.9, 25.8, 25.9, 33.3, 48.6, 63.7, 111.1, 113.4, 114.1, 134.5, 150.5, 154.8, 161.2. ESI-MS (NaCl) 337 (M+Na, 30), 315 (M+H, 100). Calculated for $C_{16}H_{22}N_6O$: C, 61.13; H, 7.05; N, 26.73. Found: C, 61.32; H, 6.95; N, 26.92.

Example 7

(Z,S)-(+)-2-Amino-6-(2-hydroxy)ethylamino-9-[(2-hydroxymethyl)cyclopropylidenemethyl]purine (12)

A mixture of compound 5 (200 mg, 0.80 mmol) and (2-hydroxy)-ethylamine (250 mg, 4.1 mmol) in ethanol (15 mL) was stirred at 50° C. for 16 h. The work-up followed the procedure described in Example 1 to give after chromatography using dichloromethane-methanol (9:1) compound 12 (171 mg, 77%).

Mp. 150-153° C. $[\alpha]^{20}_D$ 76.8° (c=0.32, N,N-dimethylformamide). $^1$H NMR (DMSO-$d_6$, 400 MHz) δ 1.14-1.18 (m, 1H), 1.42-1.46 (m, 1H), 2.05-2.09 (m, 1H), 3.30-3.53 (m, 5H), 3.68 (dd, 1H, J=10.4 Hz and 5.6 Hz), 4.82 (bs, 1H), 5.09 (bs, 1H), 5.98 (bs, 2H), 7.13 (bs, 1H), 7.18 (s, 1H), 8.32 (s, 1H). $^{13}$C NMR (DMSO-$d_6$, 100 MHz) ppm 6.9, 19.8, 43.0, 60.8, 63.7, 111.1, 113.7, 114.3, 134.8, 150.3, 155.7, 161.2. ESI-MS (NaCl+KCl) 315 (M+K, 10), 299 (M+Na, 100), 277 (M+Na, 95). Calculated for $C_{17}H_{18}N_6O$: C, 52.17; H, 5.84; N, 30.42. Found: C, 52.36; H, 5.92; N, 30.56.

Example 8

(Z,S)-(+)-2-Amino-6-propoxy-9-[(2-hydroxymethyl)cyclopropylidenemethyl]purine (13a)

A mixture of compound 5 (200 mg, 0.8 mmol), potassium carbonate (166 mg, 12 mmol), and 1-propanol (6 mL) was stirred at 70-80° C. for 16 h. The work-up followed the procedure described in Example 1 to give compound 13a (188 mg, 85%).

Mp. 147-149° C. $[\alpha]^{20}_D$ 68.3° (c=0.42, N,N-dimethylformamide). $^1$H NMR (DMSO-$d_6$, 500 MHz) δ 0.94 (t, 3H, J=7.2 Hz), 1.15-1.18 (m, 1H), 1.43-1.46 (m, 1H), 1.71-1.78 (m, 2H), 2.06-2.12 (m, 1H), 3.27-3.32 (m, 1H), 3.69-3.73 (m, 1H), 4.34 (t, 2H, J=6.8 Hz), 5.08 (t, 1H, J=5.0 Hz), 6.49 (s, 2H), 7.20 (d, 1H, J=1.5 Hz), 8.47 (s, 1H). $^{13}$C NMR (DMSO-$d_6$, 125 MHz) ppm 6.9, 10.9, 19.9, 22.5, 63.6, 68.0, 110.8, 114.1, 115.2, 137.1, 153.3, 160.8, 161.2. ESI-MS (KCl) 573 (2 M+Na, 100), 314 (M+K, 10), 298 (M+Na, 50), 276 (M+H, 10). Calculated for $C_{13}H_{17}N_5O_2$: C, 56.71; H, 6.22; N, 25.44. Found: C, 56.91; H, 6.39; N, 25.18.

Example 9

(Z,S)-(+)-2-Amino-6-pentyloxy-9-[(2-hydroxymethyl)cyclopropylidenemethyl]purine (13b)

A mixture of compound 5 (150 mg, 0.6 mmol), potassium carbonate (210 mg, 1.5 mmol), 1-pentanol (0.4 mL, 3.7 mmol) and 1,2-dimethoxyethane (10 mL) was stirred at 80° C. for 16 h. The work-up followed the procedure described in Example 1. Chromatography using dichloromethane-methanol (96:4) afforded compound 13b (155 mg, 85%).

Mp. 135-137° C. $[\alpha]^{20}_D$ 77.7° (c=0.26, N,N-dimethylformamide). $^1$H NMR (DMSO-$d_6$, 400 MHz) δ 0.87 (t, 3H, J=6.0 Hz), 1.16-1.19 (m, 1H), 1.25-1.40 (m, 4H), 1.42-1.49 (m, 1H), 1.67-1.78 (m, 2H), 2.05-2.14 (m, 1H), 3.27-3.35 (m, 1H), 3.68-3.73 (m, 1H), 4.38 (t, 2H, J=6.6 Hz), 5.07 (t, 1H, J=5.4 Hz), 6.49 (bs, 2H), 7.20 (s, 1H), 8.47 (s, 1H). $^{13}$C NMR (DMSO-$d_6$, 125 MHz) ppm 6.9, 14.6, 19.9, 22.6, 28.3, 28.8, 63.6, 66.4, 110.8, 114.1, 115.2, 137.0, 153.3, 160.8, 161.2. ESI-MS (NaCl+KCl) 645 (2M+K, 5), 629 (2 M+Na, 30), 607 (2M+H, 85), 304 (M+H, 100). Calculated for $C_{15}H_{21}N_5O_2$: C, 59.39; H, 6.98; N, 23.09. Found: C, 59.49; H, 7.02; N, 23.12.

Example 10

(Z,S)-(+)-2-Amino-6-allyloxy-9-[(2-hydroxymethyl)cyclopropylidenemethyl]purine (14)

A mixture of compound 5 (200 mg, 0.8 mmol), potassium carbonate (165 mg, 12 mmol) and allyl alcohol (5 mL) was stirred at 60-70° C. for 16 h. The work-up followed the procedure described in Example 1 to give compound 14 (172 mg, 79%).

Mp. 163-165° C. $[\alpha]^{20}_D$ 68.4° (c=0.23, N,N-dimethylformamide). $^1$H NMR (DMSO-$d_6$, 300 MHz) δ 1.15-1.20 (m, 1H), 1.43-1.49 (m, 1H), 2.07-2.02 (m, 1H), 3.26 (m, 1H), 3.68-3.75 (m, 1H), 4.94 (d, 2H, J=6.0 Hz), 5.07 (t, 1H, J=5.2 Hz), 5.25 (dd, 1H, J=7.5 and 1.8 Hz), 5.40 (dd, 1H, J=17.1 Hz, 1.8 Hz), 6.03-6.16 (m, 1H), 6.53 (s, 2H), 7.20 (d, 1H, J=1.2 Hz), 8.49 (s, 1H). $^{13}$C NMR (DMSO-$d_6$, 75 MHz) ppm 6.9, 19.9, 63.6, 66.8, 110.8, 114.0, 115.4, 118.8, 133.9, 137.3, 153.4, 160.6, 160.7. ESI-MS (NaCl) 569 (2M+Na, 100), 296 (M+Na, 48), 312 (M+K, 10), 274 (M+H, 10). Calculated for $C_{13}H_{15}N_5O_2$: C, 57.13; H, 5.53; N, 25.63. Found: C, 57.43; H, 5.44; N, 25.52.

Example 11

(Z,S)-(+)-2-Amino-6-cyclopropylmethoxy-9-[(2-hydroxymethyl)cyclopropylidenemethyl]purine (15)

A mixture of compound 5 (150 mg, 0.6 mmol), potassium carbonate (210 mg, 1.5 mmol) and cyclopropylmethanol (2 mL) in 1,2-dimethoxyethane (7 mL) was stirred at 80° C. for 16 h. The workup followed the procedure described in Example 9 to give compound 15 (142 mg, 82%).

Mp. 129-130° C. $[\alpha]^{20}_D$ 74.5° (c=0.33, N,N-dimethylformamide). $^1$H NMR (DMSO-$d_6$, 400 MHz) δ 0.34 (d, 2H, J=4.0 Hz), 0.57 (d, 2H, J=7.2 Hz), 1.16-1.20 (m, 1H), 1.25-1.33 (m, 1H), 1.47 (t, 1H, J=8.4 Hz), 2.05-2.14 (m, 1H), 3.27-3.29 (m, 1H), 3.69-3.73 (m, 1H), 4.23 (d, 2H, J=7.2 Hz), 5.06 (t, 1H, J=5.4 Hz), 6.49 (bs, 2H), 7.21 (s, 1H), 8.48 (s, 1H). $^{13}$C NMR (DMSO-$d_6$, 100 MHz) ppm 4.0, 6.9, 10.7, 19.9, 63.6, 71.1, 110.8, 114.1, 115.3, 137.1, 153.3, 160.8, 161.1. ESI-MS (NaCl+KCl) 613 (M+K, 5), 597 (2M+Na), 15), 575 (2M+1, 28), 288 (M+H, 100). Calculated for $C_{14}H_{17}N_5O_2$: C, 58.52; H, 5.96; N, 24.37. Found: C, 58.49; H, 6.03; N, 24.29.

Example 12

(Z,S)-(+)-2-Amino-6-propylthio-9-[(2-hydroxymethyl)cyclopropylidenemethyl]purine (16a)

The mixture of compound 5 (125 mg, 0.5 mmol), potassium carbonate (140 mg, 1.0 mmol), 1-propanethiol (750 mg, 10 mmol) and 1,2-dimethoxyethane (6 mL) was stirred at 50° C. for 10 h. The work-up followed the procedure described in Example 1 to give compound 16a (105 mg, 72%).

Mp. 163-164° C. $[\alpha]^{20}_D$ 77.3° (c=0.39, N,N-dimethylformamide). $^1$H NMR (DMSO-d$_6$, 500 MHz) δ 0.97 (t, 3H, J=7.5 Hz), 1.16-1.19 (m, 1H), 1.44-1.47 (m, 1H), 1.62-1.69 (m, 2H), 2.08-2.11 (m, 1H), 3.23 (t, 2H, J=7.0 Hz), 3.27-3.31 (m, 1H), 3.70-3.71 (m, 1H), 5.05 (t, 1H, J=4.0 Hz), 6.57 (s, 2H), 7.19 (s, 1H), 8.53 (s, 1H). $^{13}$C NMR (DMSO-d$_6$, 125 MHz) ppm 6.9, 13.9, 19.9, 23.4, 30.0, 63.6, 110.5, 115.8, 124.4, 138.0, 150.0, 160.4, 160.6. ESI-MS (NaCl) 605 (2M+Na, 100), 314 (M+Na, 28), 292 (M+H, 10). Calculated for $C_{13}H_{17}N_5OS$: C, 53.59; H, 5.88; N, 24.04; S, 11.00. Found: C, 53.43; H, 5.88; N, 24.30; S, 10.86.

Example 13

(Z,S)-(+)-2-Amino-6-pentylthio-9-[(2-hydroxymethyl)cyclopropylidenemethyl]purine (16b)

A mixture of compound 5 (150 mg, 0.6 mmol), potassium carbonate (170 mg, 1.2 mmol), 1-pentanethiol (374 mg, 3.60 mmol) and 1,2-dimethoxyethane (10 mL) was stirred at 80° C. for 16 h. The work-up followed the procedure described in Example 5 to give compound 16b (141 mg, 75%).

Mp. 146-147° C. $[\alpha]^{20}_D$ 82.2° (c=0.37, N,N-dimethylformamide). $^1$H NMR (DMSO-d$_6$, 400 MHz) δ 0.85 (t, 3H, J=7.2 Hz), 1.17-1.21 (m, 1H), 1.25-1.40 (m, 4H), 1.45-1.49 (m, 1H), 1.61-1.68 (m, 2H), 2.08-2.12 (m, 1H) 3.25 (t, 2H, J=7.4 Hz), 3.28-3.31 (m, 1H), 3.70-3.73 (m, 1H), 5.06 (t, 1H, J=5.2 Hz), 6.57 (bs, 2H), 7.20 (d, 1H, J=1.6 Hz), 8.54 (s, 1H). $^{13}$C NMR (DMSO-d$_6$, 100 MHz) ppm 7.0, 14.6, 19.9, 22.4, 28.1, 29.6, 31.1, 63.6, 110.5, 115.8, 124.4, 138.0, 150.0, 160.4, 160.6. ESI-MS (NaCl) 661 (2M+Na, 20), 639 (2M+H, 28), 320 (M+H, 100). Calculated for $C_{15}H_{21}N_5OS$: C, 56.40; H, 6.63; N, 21.92; S, 10.04. Found: C, 56.50; H, 6.79; N, 21.86; S, 9.96.

Example 14

(Z,S)-(+)-2-Amino-6-thio-9-[(2-hydroxymethyl)cyclopropylidenemethyl]purine (17)

A mixture of compound 5 (400 mg, 1.6 mmol) and sodium hydrosulfide hydrate (3.00 g, 53.5 mmol) in methanol (50 mL) was stirred at room temperature under nitrogen for 24 h. The solvent was evaporated, the residue was dissolved in water (40 mL) and pH of the solution was adjusted to 6 with acetic acid. The precipitate was filtered off and it washed with water. Recrystallization from methanol-water (1:1) gave compound 17 (265 mg, 67%).

Mp. 240° C. (decomposition). $[\alpha]^{20}_D$ 91.0° (c=0.26, N,N-dimethylformamide). $^1$H NMR (DMSO-d$_6$, 500 MHz) δ 1.17-1.21 (m, 1H), 1.45-1.49 (m, 1H), 2.08-2.13 (m, 1H), 3.25-3.31 (m, 1H), 3.67-3.72 (m, 1H), 5.07 (t, 1H, J=8.0 Hz), 6.86 (s, 2H), 7.09 (d, 1H, J=2.0 Hz), 8.48 (s, 1H), 11.96 (s, 1H). $^{13}$C NMR (DMSO-d$_6$, 125 MHz) ppm 6.9, 19.8, 63.4, 110.5, 116.8, 128.6, 137.9, 146.8, 153.9, 175.7. ESI-MS (NaCl+KCl) 521 (2M+Na, 50), 288 (M+K, 20), 272 (M+Na, 100), 250 (M+H, 10). Calculated for $C_{10}H_{11}N_5OS$: C, 48.18; H, 4.45; N, 28.09; S, 12.86. Found: C, 48.10; H, 4.61; N, 28.25; S, 13.02.

Example 15

(Z,S)-(+)-2-Amino-9-[(2-hydroxymethyl)cyclopropylidenemethyl]purine (18)

Compound 17 (166 mg, 0.67 mmol) was dissolved in water-methanol (1:1, 100 mL). Raney nickel (approximately 200 mg) was added and the reaction mixture was stirred at room temperature for 16 h. The catalyst was filtered off and the filtrate was evaporated. The product was chromatographed using dichloromethane-methanol (9:1) to give compound 18 (66 mg, 46%).

Mp. 185-187° C. $[\alpha]^{20}_D$ 77.7° (c=0.30, N,N-dimethylformamide). $^1$H NMR (DMSO-d$_6$, 400 MHz) δ 1.19-1.23 (m, 1H), 1.46-1.51 (m, 1H), 2.09-2.16 (m, 1H), 3.27-3.33 (m, 1H), 3.70-3.75 (m, 1H), 5.07 (dd, 1H, J=6.2 and 4.6 Hz), 6.63 (s, 2H), 7.25 (d, 1H, J=1.6 Hz), 8.60 (s, 1H), 8.68 (s, 1H). $^{13}$C NMR (DMSO-d$_6$, 100 MHz) ppm 6.9, 19.9, 63.6, 110.3, 115.7, 127.2, 140.1, 150.1, 152.0, 161.5. ESI-MS (NaCl) 457 (2M+Na, 25), 240 (M+Na, 100), 218 (M+H, 20). Calculated for $C_{10}H_{11}N_5O$: C, 55.29; H, 5.10; N, 32.24. Found: C, 55.40; H, 5.10; N, 32.19.

Example 16

In Vitro Antiviral Evaluation Methods

Cells and viruses. The routine growth and passage of KB cells was performed in monolayer cultures using minimal essential medium (MEM) with either Hanks salts [MEM(H)] or Earle salts [MEM(E)] supplemented with 10% calf serum. The sodium bicarbonate concentration was varied to meet the buffering capacity required. Cultures of diploid human foreskin fibroblasts (HFF) or MRC-5 cells were grown in medium consisting of MEM(E) with 10% fetal bovine serum. Cells were passaged at 1:2 to 1:10 dilutions according to conventional procedures by using 0.05% trypsin plus 0.02% EDTA in a HEPES buffered salt solution (HBS) (Shipman, C., Jr., *Proc. Soc. Exp. Biol.* 130:305-310 (1969)) as described previously. (Turk, S. R., et al., *Antimicrob. Agents Chemother.* 31:544-550 (1987). HFF and MRC-5 cells were passaged only at 1:2 dilutions.

Virological Procedures.

Stock HCMV was prepared by infecting HFF cells at a multiplicity of infection (m.o.i.) of <0.01 plaque-forming units (p.f.u.) per cell. Cell growth medium was changed every four days until cytopathology was evident in all cells (approximately 21 days). Supernatant fluids were retained as the virus stock. High titer HSV-1 stocks were prepared by infecting KB cells at an m.o.i. of <0.1 as detailed previously. (Turk, S. R., et al., *Antimicrob. Agents Chemother.* 31:544-550 (1987). Virus titers were determined using monolayer cultures of HFF cells for HCMV and monolayer cultures of BSC-1 cells for HSV-1 as described earlier. (Prichard, M. N. et al., *J. Virol. Methods* 28:101-106 (1990). Briefly, HFF or BSC-1 cells were planted as described above in 96-well cluster dishes and incubated overnight at 37° C. in a humidified 3% $CO_2$-97% air atmosphere. The next day cultures were inoculated with HCMV or HSV-1 and serially diluted 1:3 across the remaining eleven columns of the 96-well plate. Cultures were incubated at 37° C. for 2 hr to permit virus adsorption and then virus inoculum was replaced with 0.2 mL of fresh medium. Cultures were incubated for seven days for HCMV, two or three days for HSV-1, medium was removed, and the cell sheets were stained with 0.1% crystal violet in 20% methanol. Plaques were enumerated under 20-fold magnification in wells having the dilution which gave 5 to 20 plaques per well. Virus titers were calculated according to the following formula: Titer (p.f.u./mL)=number of plaques×5× $3^n$; where n represents the nth dilution of the virus used to infect the well in which plaques were enumerated.

Assays for Antiviral Activity.

(a) HCMV. The effect of compounds on the replication of HCMV has been measured using a plaque reduction assay. HFF cells in 24-well cluster dishes were infected with approximately 100 p.f.u. of HCMV per $cm^2$ cell sheet using the procedures detailed above. Following virus adsorption, compounds dissolved in growth medium were added to duplicate wells in three to six selected concentrations. Following incubation at 37° C. for 7 to 10 days, cell sheets were fixed, stained with crystal violet and microscopic plaques enumerated as described above. Drug effects were calculated as a percentage of reduction in number of plaques in the presence of each drug concentration compared to the number observed in the absence of drug. Ganciclovir (GCV) was used as a positive control in all experiments.

The effect of compounds on the replication of HCMV also was measured using a yield reduction assay. HFF cells were planted as described above in 96-well cluster dishes, incubated overnight, medium removed and the cultures were inoculated with HCMV at a m.o.i. of 0.5 to 1 p.f.u. per cell as reported elsewhere. After virus adsorption, inoculum was replaced with 0.2 mL of fresh medium containing test compounds. The first row of 12 wells was left undisturbed and served as virus controls. Each well in the second row received an additional 0.1 mL of medium with test compound at three times the desired final concentration. The contents of the 12 wells were mixed by repeated pipetting and then serially diluted 1:3 along the remaining wells. In this manner, six compounds could be tested in duplicate on a single plate with concentrations from 100 µM to 0.14 µM. Plates were incubated at 37° C. for seven days, subjected to one cycle of freezing and thawing; aliquots from each of the eight wells of a given column were transferred to the first column of a fresh 96-well monolayer culture of HFF cells. Contents were mixed and serially diluted 1:3 across the remaining eleven columns of the secondary plate. Each column of the original primary plate was diluted across a separate plate in this manner. Cultures were incubated, plaques were enumerated, and titers calculated as described above.

Assays for Antiviral Activity.

(b) HSV-1. An enzyme-linked immunosorbent assay (ELISA) was employed to detect HSV-1. 96-well cluster dishes were planted with BSC-1 cells at 10,000 cells per well, in a total volume of 200 µL per well of MEM(E) plus 10% calf serum. After overnight incubation at 37° C., drug and HSV-1 was added at the rate of 100 PFU/well. ELISA plates were blocked with 200 µL per well of 10% calf serum and 0.05% tween in HBS. After incubation for 30 minutes, the blocking agent was rinsed two times with HBS-T. A 1:400 dilution of AP conjugated rabbit anti-HSV-1 antibody in HBS-F was added. Plates were sealed with adhesive sheet, and incubated on rocker for one hour at 37° C. Plates were developed in the dark with 100 µL per well of substrate solution containing p-nitrophenyl phosphate. Plates were read at 492 nm. Drug effects were calculated as a percentage of the reduction in virus in the presence of each drug concentration compared to the titer obtained in the absence of drug. Acyclovir was used as a positive control in all experiments.

Cytotoxicity Assays.

Two different assays were used to explore cytotoxicity of selected compounds as we have detailed previously.
(i) Cytotoxicity produced in stationary HFF cells was determined by microscopic inspection of cells used in plaque assays which were not affected by the virus.
(ii) The effect of compounds during two population doublings of KB cells was determined by crystal violet staining and spectrophotometric quantitation of dye eluted from stained cells. (Turk, S. R., et al., *Antimicrob. Agents Chemother.* 35:1060-1065 (1991).

Data Analysis.

Dose-response relationships were constructed by linearly regressing the percent inhibition of parameters derived in the preceding sections against log drug concentrations. Fifty-percent inhibitory ($IC_{50}$) concentrations were calculated from the regression lines. Samples containing positive controls (acyclovir for HSV-1, ganciclovir for HCMV, and 2-acetylpyridine thiosemicarbazone for cytotoxicity) were used in all assays. Results from sets of assays were rejected if inhibition by the positive control deviated from its mean response by >±1.5 standard deviations.

Testing Results.

The compounds produced in Examples 1-18 exhibit a significant activity against herpes viruses. It was found that compounds of the present invention strongly inhibit the replication of HMCV as measured by plaque reduction assays using HFF as host cells by the method described above and they also inhibit the replication of HSV-1 as determined by enzyme-linked immunosorbent assay (ELISA).

TABLE 1

| Compound | IC50 (µM) HCMV [a] | IC50 (µM) HSV-1 [b] |
|---|---|---|
| 6 | 1.8 | 4 |
| 7 | 3.5 | 6 |
| 8 | 3.8 | 2.5 |
| 9 | 3.8 | 15 |
| 10 | >100 | 25 |
| 11 | >100 | 15 |
| 12 | 39 | >100 |
| 13a | 0.26 | 1 |
| 13b | 0.21 | 7 |
| 14 | 0.33 | 1.5 |
| 15 | 0.32 | 7 |
| 16a | 0.22 | 1 |
| 16b | 0.32 | 7 |
| 17 | 37 | >100 |
| 18 | >100 | 35 |
| Control | 4.1 [c] | 0.15 [d] |

[a] Plaque reduction assy.
[b] ELISA.
[c] Ganciclovir.
[d] Acyclovir.

Compounds of the present invention were also tested for cytotoxicity in cultures of HFF and KB cells according to the methods described above. These tests have indicated a complete lack of cytotoxicity of tested compounds.

TABLE 2

| Compound | $IC_{50}$ (µM) Stationary HFF cells | $IC_{50}$ (µM) Growing KB cells |
|---|---|---|
| 6 | >100 | >100 |
| 7 | >100 | >100 |

TABLE 2-continued

| Compound | IC$_{50}$ (μM) Stationary HFF cells | IC$_{50}$ (μM) Growing KB cells |
|---|---|---|
| 8 | >100 | >100 |
| 9 | >100 | >100 |
| 10 | >100 | >100 |
| 11 | >100 | >100 |
| 12 | >100 | >100 |
| 13a | >100 | >100 |
| 13b | >100 | >100 |
| 14 | >100 | >100 |
| 15 | >100 | >100 |
| 16a | >100 | >100 |
| 16b | >100 | >100 |
| 17 | >100 | >100 |
| 18 | >100 | >100 |
| Control | >100 [a] | >100 [b] |

[a] Ganciclovir.
[b] Acyclovir.

We claim:

1. A method of treating a mammal infected with a virus selected from the group consisting of a cytomegalovirus (CMV), herpes simplex virus-1 (HSV-1), herpes simplex virus-2 (HSV-2), human herpes virus-6 (HHV-6), human herpes virus-7 (HHV-7), human herpes virus-8 (HHV-8), and hepatitis B virus (HBV) comprising the step of administering to said mammal an effective amount of:

a compound having Formula 1 or Formula 2:

wherein B is 2-aminopurine-9-yl, unsubstituted or substituted at the 6 position with NHR$_1$, OR$_2$, or SR$_3$;

R$_1$ is selected from the group consisting of alkenyl, alkynyl, and benzyl, any of which may be optionally substituted with one or more members of the group consisting of hydroxy, halo, amino, acyl, cycloalkyl, heterocyclyl and aryl;

R$_2$ is selected from the group consisting of alkenyl, alkynyl, and cycloalkyl, any of which may be branched or unbranched and optionally substituted with one or more members of the group consisting of hydroxy, halo, amino, acyl, cycloalkyl, heterocyclyl, and aryl; and R$_3$ is selected from the group consisting of alkyl, alkenyl, alkynyl, and cycloalkyl, any of which may be branched or unbranched and optionally substituted with one or more members of the group consisting of hydroxy, halo, amino, acyl, cycloalkyl, heterocyclyl and aryl;

or a compound having Formula 3 or Formula 4:

wherein X is O;

R$_1$ and R$_2$ are alkyl or aryl; or R$_1$X or R$_2$X is an amino acid residue with X as NH;

B is 2-aminopurine-9-yl, which is unsubstituted or substituted at the 6 position with NHR$_4$, OR$_5$, or SR$_6$;

R$_4$ is selected from the group consisting of alkenyl, and alkynyl, any of which may be optionally substituted with one or more members of the group consisting of hydroxy, halo, amino, acyl, cycloalkyl, heterocyclyl and aryl;

R$_5$ is selected from the group consisting of alkenyl, alkynyl, and cycloalkyl, any of which may be branched or unbranched and optionally substituted with one or more members of the group consisting of hydroxy, halo, amino, acyl, cycloalkyl, heterocyclyl and aryl;

R$_6$ is selected from the group consisting of alkyl, alkenyl, alkynyl, and cycloalkyl, any of which may be branched or unbranched and optionally substituted with one or more members of the group consisting of hydroxy, halo, amino, acyl, cycloalkyl, heterocyclyl and aryl;

or a combination thereof.

2. The method of claim 1, wherein B is substituted at the 6 position with NHR$_1$, OR$_2$, or SR$_3$, wherein:

R$_1$ is selected from the group consisting of C$_3$-C$_8$ alkenyl, and C$_3$-C$_8$ alkynyl, any of which may be optionally substituted with one or more members of the group consisting of hydroxy, halo, amino, acyl, cycloalkyl, heterocyclyl and aryl;

R$_2$ is selected from the group consisting of C$_3$-C$_8$ alkenyl, C$_3$-C$_8$ alkynyl, and C$_3$-C$_{10}$ cycloalkyl, any of which may be branched or unbranched and optionally substituted with one or more members of the group consisting of hydroxy, halo, amino, acyl, cycloalkyl, heterocyclyl and aryl;

and

R$_3$ is selected from the group consisting of C$_{2-8}$ alkyl, C$_3$-C$_8$ alkenyl, C$_3$-C$_8$ alkynyl, and C$_{3-10}$ cycloalkyl, any of which may be branched or unbranched and optionally substituted with one or more members of the group consisting of hydroxy, halo, amino, acyl, cycloalkyl, heterocyclyl and aryl.

3. The method of claim 1, wherein B is 2-aminopurine-9-yl, which is substituted in the 6 position with NHR$_1$, OR$_2$, or SR$_3$, wherein:

R$_1$ is selected from the group consisting of C$_3$-C$_6$ alkenyl, and C$_3$-C$_6$ alkynyl, any of which may be optionally substituted with one or more members of the group consisting cycloalkyl, heterocyclyl and aryl;

R$_2$ is selected from the group consisting of C$_3$-C$_6$ alkenyl, C$_3$-C$_6$ alkynyl, and C$_{3-8}$ cycloalkyl, any of which may be branched or unbranched and optionally substituted with one or more members of the group consisting of cycloalkyl, heterocyclyl, and aryl; and R$_3$ is selected from the group consisting of C$_{2-6}$ alkyl, C$_3$-C$_6$ alkenyl, C$_3$-C$_6$ alkynyl, and C$_{3-8}$ cycloalkyl, any of which may be branched or unbranched and optionally substituted with one or more members of the group consisting of hydroxy, halo, amino, acyl, cycloalkyl, heterocyclyl and aryl.

4. The method of claim 1, wherein the compound is selected from the group consisting of (Z,S)-(+)-2-amino-6-allylamino-9-[(2-hydroxymethyl)cyclopropylidenemethyl]purine; (Z,S)-(+)-2-amino-6-propargylamino-9-[(2-hydroxymethyl)cyclo-propylidenemethyl]purine; (Z,S)-(+)-2-amino-6-isopropylamino-9-[(2-hydroxymethyl)cyclopropylidenemethyl]purine; (Z,S)-(+)-2-amino-6-benzylamino 9-[(2-hydroxymethyl)cyclopropylidenemethyl]purine; (Z,S)-(+)-2-amino-6-cyclohexylamino-9-[(2-hydroxymethyl)cyclopropylidenemethyl]purine; (Z,S)-(+)-2-amino-6-(2-hydroxyl)ethylamino-9-[(2-hydroxymethyl)cyclopropylidenemethyl]purine; (Z,S)-(+)-2-amino-6-allyloxy-9-[(2-hydroxymethyl)cyclopropylidenemethyl]purine; (Z,S)-(+)-2-amino-6-cyclopropylmethoxy-9-[(2-hydroxymethyl)cyclopropylidenemethyl]purine; (Z,S)-(+)-2-amino-6-propylthio 9-[(2-hydroxymethyl)cyclopropylidenemethyl]purine; (Z,S)-(+)-2-amino6-pentylthio-9-[(2-hydroxymethyl)cyclopropylidene-methyl]purine; and (Z,S)-(+)-2-amino-9-[(2-hydroxymethyl)cyclopropylidenemethyl]purine.

5. The method of claim 1, wherein B is 2-aminopurine-9-yl, which is substituted at the 6 position with NHR$_4$, OR$_5$, or SR$_6$, wherein:

R$_4$ is selected from the group consisting of C$_3$-C$_8$ alkenyl, and C$_3$-C$_8$ alkynyl, any of which may be optionally substituted with one or more members of the group consisting of hydroxy, halo, amino, acyl, cycloalkyl, heterocyclyl and aryl;

R$_5$ is selected from the group consisting of C$_3$-C$_8$ alkenyl, C$_3$-C$_8$ alkynyl, and C$_{3-10}$ cycloalkyl, any of which may be branched or unbranched and optionally substituted with one or more members of the group consisting of hydroxy, halo, amino, acyl, cycloalkyl, heterocyclyl, and aryl; and R$_6$ is selected from the group consisting of C$_2$ alkyl, C$_3$-C$_8$ alkenyl, C$_3$-C$_8$ alkynyl, and C$_{3-10}$ cycloalkyl, any of which may be branched or unbranched and optionally substituted with one or more members of the group consisting of hydroxy, halo, amino, acyl, cycloalkyl, heterocyclyl and aryl.

6. The method of claim 1, wherein B is 2-aminopurine-9-yl, which is substituted in the 6 position with NHR$_4$, OR$_5$, or SR$_6$, wherein:

R$_4$ is selected from the group consisting of C$_3$-C$_6$ alkenyl, and C$_3$-C$_6$ alkynyl, any of which may be optionally substituted with one or more members of the group consisting cycloalkyl, heterocyclyl and aryl;

R$_5$ is selected from the group consisting of C$_3$-C$_6$ alkenyl, C$_3$-C$_6$ alkynyl, and C$_{3-8}$ cycloalkyl, any of which may be branched or unbranched and optionally substituted with one or more members of the group consisting of cycloalkyl, heterocyclyl, and aryl; and R$_6$ is selected from the group consisting of C$_{2-6}$ alkyl, C$_3$-C$_6$ alkenyl, C$_3$-C$_6$ alkynyl, and C$_{3-8}$ cycloalkyl, any of which may be branched or unbranched and optionally substituted with one or more members of the group consisting of hydroxy, halo, amino, acyl, cycloalkyl, heterocyclyl and aryl.

7. The method of any one of claims 1-6, wherein said mammal is a human.

8. The method of any one of claims 1-6, further comprising a step of administering an additional compound.

9. The method of claim 8, wherein said additional compound is selected from the group consisting of acyclovir, ganciclovir, zidovudine, AZT, ddI, ddC, 3TC, d4T, and combinations thereof.

10. The method of claim 1, wherein the virus is selected from the group consisting of a cytomegalovirus (CMV), herpes simplex virus-1 (HSV-1) and herpes simplex virus-2 (HSV-2).

11. A method of reducing viral replication in a mammal infected with a virus selected from the group consisting of a cytomegalovirus (CMV), herpes simplex virus-1 (HSV-1), herpes simplex virus-2 (HSV-2), human herpes virus-6 (HHV-6), human herpes virus-7 (HHV-7), human herpes virus-8 (HHV-8), and hepatitis B virus (HBV) comprising the step of administering to said mammal an effective amount of:

a compound having Formula 1 or Formula 2:

Formula 1

Formula 2 wherein B is 2-aminopurine-9-yl, unsubstituted or substituted at the 6 position with NHR$_1$, OR$_2$, or SR$_3$;

R$_1$ is selected from the group consisting of alkenyl, alkynyl, and benzyl, any of which may be optionally substituted with one or more members of the group consisting of hydroxy, halo, amino, acyl, cycloalkyl, heterocyclyl and aryl;

R$_2$ is selected from the group consisting of alkenyl, alkynyl, and cycloalkyl, any of which may be branched or unbranched and optionally substituted with one or more members of the group consisting of hydroxy, halo, amino, acyl, cycloalkyl, heterocyclyl, and aryl; and R$_3$ is selected from the group consisting of alkyl, alkenyl, alkynyl, and cycloalkyl, any of which may be branched or unbranched and optionally substituted with one or more members of the group consisting of hydroxy, halo, amino, acyl, cycloalkyl, heterocyclyl and aryl;

or a compound having Formula 3 or Formula 4:

Formula 3

-continued

Formula 4 wherein X is O;
R₁ and R₂ are alkyl or aryl; or R₁X or R₂X is an amino acid residue with X as NH;
B is 2-aminopurine-9-yl, which is unsubstituted or substituted at the 6 position with NHR₄, OR₅, or SR₆;
R₄ is selected from the group consisting of alkenyl, and alkynyl, any of which may be optionally substituted with one or more members of the group consisting of hydroxy, halo, amino, acyl, cycloalkyl, heterocyclyl and aryl;
R₅ is selected from the group consisting of alkenyl, alkynyl, and cycloalkyl, any of which may be branched or unbranched and optionally substituted with one or more members of the group consisting of hydroxy, halo, amino, acyl, cycloalkyl, heterocyclyl and aryl;
R₆ is selected from the group consisting of alkyl, alkenyl, alkynyl, and cycloalkyl, any of which may be branched or unbranched and optionally substituted with one or more members of the group consisting of hydroxy, halo, amino, acyl, cycloalkyl, heterocyclyl and aryl;
or a combination thereof.

12. The method of claim 11, wherein B is substituted at the 6 position with NHR₁, OR₂, or SR₃, wherein:
R₁ is selected from the group consisting of $C_3$-$C_8$ alkenyl, and $C_3$-$C_8$ alkynyl, any of which may be optionally substituted with one or more members of the group consisting of hydroxy, halo, amino, acyl, cycloalkyl, heterocyclyl and aryl;
R₂ is selected from the group consisting of $C_3$-$C_8$ alkenyl, $C_3$-$C_8$ alkynyl, and $C_{3-10}$ cycloalkyl, any of which may be branched or unbranched and optionally substituted with one or more members of the group consisting of hydroxy, halo, amino, acyl, cycloalkyl, heterocyclyl and aryl; and
R₃ is selected from the group consisting of $C_{2-8}$ alkyl, $C_3$-$C_8$ alkenyl, $C_3$-$C_8$ alkynyl, and $C_{3-10}$ cycloalkyl, any of which may be branched or unbranched and optionally substituted with one or more members of the group consisting of hydroxy, halo, amino, acyl, cycloalkyl, heterocyclyl and aryl.

13. The method of claim 11, wherein B is 2-aminopurine-9-yl, which is substituted in the 6 position with NHR₁, OR₂, or SR₃, wherein:
R₁ is selected from the group consisting of $C_3$-$C_6$ alkenyl, and $C_3$-$C_6$ alkynyl, any of which may be optionally substituted with one or more members of the group consisting cycloalkyl, heterocyclyl and aryl;
R₂ is selected from the group consisting of $C_3$-$C_6$ alkenyl, $C_3$-$C_6$ alkynyl, and $C_{3-10}$ cycloalkyl, any of which may be branched or unbranched and optionally substituted with one or more members of the group consisting of cycloalkyl, heterocyclyl, and aryl; and
R₃ is selected from the group consisting of $C_{2-6}$ alkyl, $C_3$-$C_6$ alkenyl, $C_3$-$C_6$ alkynyl, and $C_{3-8}$ cycloalkyl, any of which may be branched or unbranched and optionally substituted with one or more members of the group consisting of hydroxy, halo, amino, acyl, cycloalkyl, heterocyclyl and aryl.

14. The method of claim 11, wherein the compound is selected from the group consisting of (Z,S)-(+)-2-amino-6-allylamino-9-[(2-hydroxymethyl)cyclopropylidenemethyl]purine; (Z,S)-(+)-2-amino-6-propargylamino-9-[(2-hydroxymethyl)cyclo-propylidenemethyl]purine; (Z,S)-(+)-2-amino-6-isopropylamino-9-[(2-hydroxymethyl)cyclopropylidenemethyl]purine; (Z,S)-(+)-2-amino-6-benzylamino 9-[(2-hydroxymethyl)cyclopropylidenemethyl]purine; (Z,S)-(+)-2-amino-6-cyclohexylamino-9-[(2-hydroxymethyl)cyclopropylidenemethyl]purine; (Z,S)-(+)-2-amino-6-(2-hydroxyl)ethylamino-9-[(2-hydroxymethyl)cyclopropylidenemethyl]purine; (Z,S)-(+)-2-amino-6-allyloxy-9-[(2-hydroxymethyl)cyclopropylidenemethyl]purine; (Z,S)-(+)-2-amino-6-cyclopropylmethoxy-9-[(2-hydroxymethyl)cyclopropylidenemethyl]purine; (Z,S)-(+)-2-amino-6-propylthio 9-[(2-hydroxymethyl)cyclopropylidenemethyl]purine; (Z,S)-(+)-2-amino6-pentylthio-9-[(2-hydroxymethyl)cyclopropylidene-methyl]purine; and (Z,S)-(+)-2-amino-9-[(2-hydroxymethyl)cyclopropylidenemethyl]purine.

15. The method of claim 11, wherein B is 2-aminopurine-9-yl, which is substituted at the 6 position with NHR₄, OR₅, or SR₆, wherein:
R₄ is selected from the group consisting of $C_3$-$C_8$ alkenyl, and $C_3$-$C_8$ alkynyl, any of which may be optionally substituted with one or more members of the group consisting of hydroxy, halo, amino, acyl, cycloalkyl, heterocyclyl and aryl;
R₅ is selected from the group consisting of $C_3$-$C_8$ alkenyl, $C_3$-$C_8$ alkynyl, and $C_{3-10}$ cycloalkyl, any of which may be branched or unbranched and optionally substituted with one or more members of the group consisting of hydroxy, halo, amino, acyl, cycloalkyl, heterocyclyl, and aryl; and
R₆ is selected from the group consisting of $C_2$ alkyl, $C_3$-$C_8$ alkenyl, $C_3$-$C_8$ alkynyl, and $C_{3-10}$ cycloalkyl, any of which may be branched or unbranched and optionally substituted with one or more members of the group consisting of hydroxy, halo, amino, acyl, cycloalkyl, heterocyclyl and aryl.

16. The method of claim 11, wherein B is 2-aminopurine-9-yl, which is substituted in the 6 position with NHR₄, OR₅, or SR₆, wherein:
R₄ is selected from the group consisting of $C_3$-$C_6$ alkenyl, and $C_3$-$C_6$ alkynyl, any of which may be optionally substituted with one or more members of the group consisting cycloalkyl, heterocyclyl and aryl;
R₅ is selected from the group consisting of $C_3$-$C_6$ alkenyl, $C_3$-$C_6$ alkynyl, and $C_{3-8}$ cycloalkyl, any of which may be branched or unbranched and optionally substituted with one or more members of the group consisting of cycloalkyl, heterocyclyl, and aryl; and
R₆ is selected from the group consisting of $C_{2-6}$ alkyl, $C_3$-$C_6$ alkenyl, $C_3$-$C_6$ alkynyl, and $C_{3-8}$ cycloalkyl, any of which may be branched or unbranched and optionally substituted with one or more members of the group consisting of hydroxy, halo, amino, acyl, cycloalkyl, heterocyclyl and aryl.

17. The method of any one of claims 11-16, wherein said mammal is a human.

18. The method of any one of claims 11-16, further comprising a step of administering an additional compound.

19. The method of claim 18, wherein said additional compound is selected from the group consisting of acyclovir, ganciclovir, zidovudine, AZT, ddI, ddC, 3TC, d4T, and combinations thereof.

* * * * *